US009228938B2

(12) United States Patent
Hager et al.

(10) Patent No.: US 9,228,938 B2
(45) Date of Patent: Jan. 5, 2016

(54) METHOD AND DEVICE FOR REMOTE SENSING OF AMOUNT OF INGREDIENTS AND TEMPERATURE OF GASES

(71) Applicant: Hager Environmental and Atmospheric Technologies, LLC, Knoxville, TN (US)

(72) Inventors: J. Stewart Hager, Knoxville, TN (US); Geoffrey Yerem, Knoxville, TN (US)

(73) Assignee: HAGER ENVIRONMENTAL AND ATMOSPHERIC TECHNOLOGIES, LLC, Knoxville, TN (US)

( * ) Notice: Subject to any disclaimer, the term of this patent is extended or adjusted under 35 U.S.C. 154(b) by 0 days.

(21) Appl. No.: 14/180,512

(22) Filed: Feb. 14, 2014

(65) Prior Publication Data

US 2014/0160479 A1    Jun. 12, 2014

Related U.S. Application Data

(63) Continuation-in-part of application No. 13/689,406, filed on Nov. 29, 2012, now Pat. No. 8,654,335, which is a continuation-in-part of application No. 12/883,621, filed on Sep. 16, 2010, now Pat. No. 8,330,957, which is a continuation-in-part of application No. 12/493,634, filed on Jun. 29, 2009, now Pat. No. 8,134,711.

(51) Int. Cl.
*G01N 21/00* (2006.01)
*G01N 21/3504* (2014.01)
(Continued)

(52) U.S. Cl.
CPC .... *G01N 21/3504* (2013.01); *G01N 2021/1793* (2013.01); *G01N 2021/1795* (2013.01); *G01N 2021/399* (2013.01)

(58) Field of Classification Search
CPC .......................................... G01N 21/00
USPC .......................................... 356/438
See application file for complete search history.

(56) References Cited

U.S. PATENT DOCUMENTS 4,924,095 A * 5/1990 Swanson, Jr. ............... 250/338.5
5,319,199 A * 6/1994 Stedman et al. ............ 250/338.5
(Continued)

FOREIGN PATENT DOCUMENTS

| CN | 1412541 A | 4/2003 |
|---|---|---|
| WO | 2007/082426 A1 | 7/2007 |
| WO | 2010026579 A2 | 3/2010 |
| WO | 2012/002979 A1 | 1/2012 |

OTHER PUBLICATIONS

The Extended European Search Report, European Patent Office (EPO), Feb. 26, 2014.
(Continued)

*Primary Examiner* — Roy M Punnoose
(74) *Attorney, Agent, or Firm* — Tim Tingkang Xia; Locke Lord LLP

(57) ABSTRACT

Aspects of the invention are directed to a device and method for detecting characteristics of a gas. The gas includes an exhausted plume from a vehicle or factory plant, leaked gas from an oil well or gas resource, or unidentified gas from an unknown source. The method includes sweepingly directing a beam of light through the gas to a target surface on which the beam of light is scattered, acquiring the scattered light scattered from the target surface, and processing the acquired scattered light to determine the characteristics of the gas, where the characteristics of the gas comprise at least one of a temperature of the gas and an amount of at least one ingredient of the gas.

12 Claims, 9 Drawing Sheets

(51) Int. Cl.
*G01N 21/17* (2006.01)
*G01N 21/39* (2006.01)

(56) References Cited

U.S. PATENT DOCUMENTS

| | | | | |
|---|---|---|---|---|
| 5,489,777 | A * | 2/1996 | Stedman et al. | 250/338.5 |
| 5,498,872 | A * | 3/1996 | Stedman et al. | 250/338.5 |
| 5,726,450 | A | 3/1998 | Peterson et al. | |
| 6,230,087 | B1 | 5/2001 | Didomenico et al. | |
| 6,455,851 | B1 * | 9/2002 | Lord et al. | 250/338.5 |
| 6,542,831 | B1 * | 4/2003 | Moosmuller et al. | 702/40 |
| 7,183,945 | B2 * | 2/2007 | DiDomenico et al. | 340/937 |
| 7,952,047 | B2 * | 5/2011 | Gevelber et al. | 219/121.47 |
| 8,134,711 | B2 * | 3/2012 | Hager | 356/446 |
| 8,330,957 | B2 * | 12/2012 | Hager | 356/438 |
| 2004/0104345 | A1 * | 6/2004 | Kansakoski et al. | 250/338.5 |
| 2007/0164220 | A1 * | 7/2007 | Luk | 250/338.5 |
| 2008/0297360 | A1 * | 12/2008 | Knox et al. | 340/628 |

OTHER PUBLICATIONS

The Office Action and Search Report, State Intellectual Property Office of the People's Republic of China (SIPO), Jan. 6, 2015.

Ling, Bo et al., "A Practical and Inexpensive System for Natural Gas Leak Remote Detection", ISA EXPO Technical Conference, Oct. 2006, Houston.

Reichardt, Thomas A. et al., "Evaluation of Active and Passive Gas Imagers for Transmission Pipeline Remote Leak Detection", Final Report, Dec. 2002.

The Patent Examination Report No. 1 for Australian Patent Application No. 2010356303, IP Australian, Feb. 14, 2014.

The Patent Examination Report No. 2 for Australian Patent Application No. 2010356303, IP Australian, Feb. 17, 2015.

The EP Office Action for EP Patent Application No. 10 854 238.2, European Patent Office, May 6, 2015.

* cited by examiner

METHOD AND DEVICE FOR REMOTE SENSING OF AMOUNT OF INGREDIENTS AND TEMPERATURE OF GASES

CROSS-REFERENCE TO RELATED PATENT APPLICATIONS

This application is a continuation-in-part of U.S. patent application Ser. No. 13/689,406, filed Nov. 29, 2012, entitled "METHOD AND DEVICE FOR QUANTIFICATION OF GASES IN PLUMES BY REMOTE SENSING," by J. Stewart Hager et al., now U.S. Pat. No. 8,654,335, which itself is a continuation-in-part of U.S. patent application Ser. No. 12/883,621, filed Sep. 16, 2010, entitled "DEVICE AND METHOD FOR QUANTIFICATION OF GASES IN PLUMES BY REMOTE SENSING," by J. Stewart Hager, now U.S. Pat. No. 8,330,957, which itself is a continuation-in-part of U.S. patent application Ser. No. 12/493,634, filed Jun. 29, 2009, entitled "DEVICE FOR REMOTE SENSING OF VEHICLE EMISSION," by J. Stewart Hager, now U.S. Pat. No. 8,134,711. Each of the above disclosures is incorporated herein in its entirety by reference.

Some references, which may include patents, patent applications and various publications, are cited and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference were individually incorporated by reference.

FIELD OF THE INVENTION

The invention generally relates to remote detection of gas emission or leakage, and more particularly to methods and devices that utilize optical masses for detecting amounts of ingredients and temperature of gases.

BACKGROUND OF THE INVENTION

The background description provided herein is for the purpose of generally presenting the context of the present invention. Work of the presently named inventors, to the extent it is described in this background section, as well as aspects of the description that may not otherwise qualify as prior art at the time of filing, are neither expressly nor impliedly admitted as prior art against the present invention.

It is known that vehicle emissions are a major contributor to air pollution. In order to identify vehicles that are releasing excessive polluting emissions, many countries mandate annual vehicle emission inspections. To this purpose various vehicle emission inspection systems have been developed. Generally, these systems can be very expensive, and their operation can require a vast amount of labor and skill. Additionally, emission inspection systems have traditionally been operated in testing stations where the emissions are measured when the test vehicle is idling or running under artificially loaded conditions. Although such measurements provide general baseline information regarding a vehicle's emissions and state of repair, it is not necessarily representative of "real world" driving conditions.

Recently, remote emission sensing systems have been developed for detecting emissions of vehicles as they are driving on the road. For example, U.S. Pat. Nos. 5,319,199 and 5,498,872 to Stedman et al. discloses a remote sensing system in which the light source 1110 and detector 1130 are oppositely located on both sides of the road 1101, respectively, as shown in FIG. 9(a). For such an arrangement, a beam of light 1115 generated from the source 1110 passes through an exhaust plume 1140 emitted from a vehicle 1105 driven on the road 1101, thereby carrying an absorption signal associated with components and concentrations of the exhaust plume 1140. The beam 1115 is collected by the detector 1130 for analyzing the components and concentrations of exhaust plume 1140. Alternatively, as shown in FIG. 9(b), the light source 1110 and detector 1130 are located on the same side of the road 1101. And two reflectors 1150 located on the opposite side of the road 1101 are used to reflect the beam 1115 generated from the source 1110 to the detector 1130 with two passes through the vehicle exhaust plume 1140, which increases the absorption signal. This system measures only part of the plume and has to ratio the $CO_2$ measurements to all other pollutants to get relative values. It does not measure the amount left behind or absolute values. Furthermore, for such remote emission sensing systems, the source, detector and reflectors are set up on both sides of the road, and much care needs to be taken during their installation and maintenance. Additionally, such a system is difficult to operate with more than one lane of traffic particularly when more than one vehicle passes through the detector simultaneously.

Current vehicle remote-sensing systems only sense part of the exhaust plume. If the infrared beams are large enough or use multi-pass beams with respect to the size of the plume they will encompass the entire plume. Since the entire plume is being sensed, then one can calculate absolute amounts and get grams-per-mile directly.

Conventionally, a non-dispersive infrared system usually uses an infrared beam 2 to 3 inches in diameter. The beam is directed across the road and reflected back through a series of mirrors. The system therefore only senses a percentage of the gases in the entire cross-section of the plume. The system then uses ratios to carbon dioxide to calculate the combustion equation. The combustion equation then gives you tailpipe percentages. Therefore, in order to get grams per mile one must calculate the vehicle specific power (VSP) and know model and make of the vehicle.

Further, when a vehicle starts up, the emissions mitigation system on the vehicle usually takes a warm-up time to warm up to a minimum temperature. The warm-up time is generally a minute or so, but can be much longer. Until the emission mitigation system reaches the minimum temperature, the exhaust plume may have carbon monoxide (CO), nitric oxide (NO), hydrocarbons and other pollutant above expectable levels such that the vehicle is not able to pass a typical emission test. Thus, if a vehicle is tested with a remote sensing device when it is cold (i.e. before the vehicle warms up), the remote sensing device will give a false negative reading. Current remote sensing devices are unable to identify such false negative readings from the real negative readings without the help of infrared cameras. Infrared cameras are used to see the reflection of a hot engine off the road surface and are costly separate units. Accordingly, current remote sensing devices are required to measure one vehicle with negative readings for at least 3 times at different locations to justify marking the vehicle as a dirty vehicle, as the chance of the same vehicle being cold in different locations and occasions are remote.

Therefore, a heretofore unaddressed need exists in the art to address the aforementioned deficiencies and inadequacies.

SUMMARY OF THE INVENTION

One aspect of the present invention is directed to a device for detecting characteristics of a gas. The gas includes an exhausted plume from a vehicle or factory plant, leaked gas from an oil well or gas resource, or unidentified gas from an unknown source. In one embodiment, the method includes sweepingly directing a beam of light through the gas to a target surface on which the beam of light is scattered, acquiring the scattered light scattered from the target surface, and processing the acquired scattered light to determine the characteristics of the gas, where the characteristics of the gas comprise at least one of a temperature of the gas and an amount of at least one ingredient of the gas. The target surface can be one of a road surface of a road having at least one lane, a drill surface of oil well or gas resource and a surface having the unidentified gas.

In one embodiment, the acquiring step comprises acquiring an image from the scattered light.

In one embodiment, the processing step comprises obtaining a plurality of pixels from the acquired image, each pixel having a pixel area projected onto the road, wherein each of the at least one lane of the road correspond to a group of the pixels, characterizing an absorption rate of light of each pixel from the acquired image, calculating optical mass of each pixel from the characterized absorption rate of the pixel, and for each of the at least one lane, identifying whether the gas exists on the lane based on the optical mass of the corresponding group of the pixels.

In one embodiment, the processing step comprises characterizing an absorption line from the acquired scattered light, obtaining a half-width at half-maximum (HWHM) of the absorption line, and determining the temperature of the gas from the obtained HWHM with a relationship of:

$$T_{gas} = T_0 \left[ \frac{b_L^0(T_0)}{b_L^0(T_{gas})} \right]^{\frac{1}{n}},$$

where $T_{gas}$ is the temperature of the gas, $T_0$ is a standard temperature, $b_L^0(T_0)$ is a standard HWHM corresponding to the standard temperature, $b_L^0(T_{gas})$ is the obtained HWHM, and n is a coefficient of temperature dependence of an air-broadened half-width.

In one embodiment, the HWHM is obtained from the absorption line of the exhausted gas/plume with low ambient concentration. In one embodiment, the exhausted gas/plume with low ambient concentration is carbon monoxide (CO) or nitric oxide (NO).

In one embodiment, the directing step comprises spin-sweepingly directing the beam of light along an optical path to the target surface such that the optical path spin-forms a cone geometry covering the target surface. In one embodiment, the processing step comprises processing the acquired scattered light to obtain information corresponding to the cone geometry, identifying whether the gas exists in the cone geometry based on the information corresponding to the cone geometry, and if the gas exists, determining at least one of a location of the gas on the target surface, a flow rate of the gas, at least one ingredient of the gas, and an absolute amount of the gas.

In another aspect, the present invention relates to a device for detecting characteristics of a gas. The gas can be an exhausted plume from a vehicle or factory plant, leaked gas from an oil well or gas resource, or any unidentified gas from an unknown source.

In one embodiment, the device includes a light source configured to emit a beam of light through the gas to a target surface on which the beam of light is scattered, a detector configured to acquire the scattered light scattered from the surface, and a processor configured to process the acquired scattered light to determine the characteristics of the gas, wherein the characteristics of the gas comprise at least one of a temperature of the gas and an amount of at least one ingredient of the gas. The target surface is one of a road surface of a road having at least one lane, a drill surface of oil well or gas resource and a surface having the unidentified gas.

In one embodiment, the device includes further includes a positioning optics configured to sweepingly direct the beam of light emitted by the light source through the gas to the target surface.

In one embodiment, the detector is configured to acquire an image from the scattered light, and the processor is configured to process the acquired image to perform functions of obtaining a plurality of pixels from the acquired image, each pixel having a pixel area projected onto the road, wherein each of the at least one lane of the road correspond to a group of the pixels, characterizing an absorption rate of light of each pixel from the acquired image, calculating optical mass of each pixel from the characterized absorption rate of the pixel, and for each of the at least one lane, identifying whether the gas exists on the lane based on the optical mass of the corresponding group of the pixels.

In one embodiment, the processor is configured to determine the temperature of the gas by characterizing an absorption line from the acquired scattered light, obtaining a half-width at half-maximum (HWHM) of the absorption line, and determining the temperature of the gas from the obtained HWHM with a relationship of:

$$T_{gas} = T_0 \left[ \frac{b_L^0(T_0)}{b_L^0(T_{gas})} \right]^{\frac{1}{n}},$$

wherein $T_{gas}$ is the temperature of the gas, $T_0$ is a standard temperature, $b_L^0(T_0)$ is a standard HWHM corresponding to the standard temperature, $b_L^0(T_{gas})$ is the obtained HWHM, and n is a coefficient of temperature dependence of an air-broadened half-width.

In one embodiment, the HWHM is obtained from the absorption line of the exhausted gas/plume with low ambient concentration. In one embodiment, the exhausted gas/plume with low ambient concentration is carbon monoxide (CO) or nitric oxide (NO).

In addition, the device may also have a positioning optics configured to spin-sweepingly direct the beam of light through the gas to the target surface such that an optical path between the positioning optics and the target surface spin-forms a cone geometry covering the target surface. In one embodiment, the positioning optics comprises an X-Y galvanometer or a spinning mirror.

In one embodiment, the processor is configured to perform functions of processing the acquired scattered light to obtain information corresponding to the cone geometry, identifying whether the gas exists in the cone space based on the information corresponding to the cone geometry, and if the gas leak exists, determining at least one of a position of the gas on the target surface, a flow rate of the gas, at least one ingredient of the gas, and an absolute amount of the gas.

These and other aspects of the invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
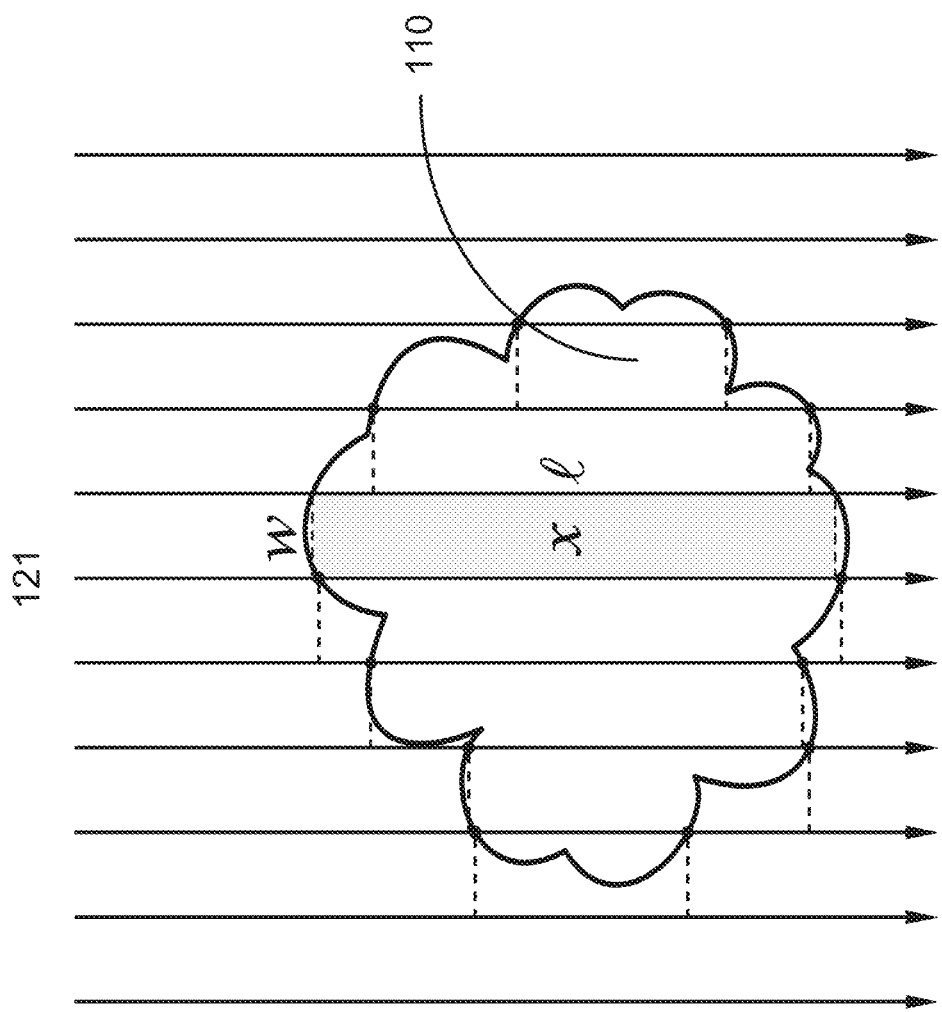
FIG. 1 illustrates schematically a method for quantifying absolute amounts of ingredients of a plume sampled with a discrete number of equally spaced, infinitesimally thin beams of parallel light according to one embodiment of the invention.

The invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about", substantially, or "approximately" shall generally mean within 20 percent, preferably within 10 percent, and more preferably within 5 percent of a given value or range. Numerical quantities given herein are approximate, meaning that the term "around", "about", substantially, or "approximately" can be inferred if not expressly stated.

As used herein, the term "LIDAR" is an acronym or abbreviation of "light detection and ranging", and is an optical remote sensing technology that measures properties of scattered light to find range and/or other information of a distant target. Differential Absorption LIDAR (DIAL) is a commonly used technique to measure column abundances of gases in the atmosphere.

As used herein, the term "EDAR" is an acronym or abbreviation of "emission detection and reporting", and is an emission sensing technology that measures properties of emission to find range and/or other information of a distant emission.

As used herein, the term "optical mass" is a measure of the total number of absorbing molecules per unit area occurring along the direction of propagation of the radiation in a gas sample.

As used herein, the terms "comprising," "including," "having," "containing," "involving," and the like are to be understood to be open-ended, i.e., to mean including but not limited to.

The description will be made as to the embodiments of the invention in conjunction with the accompanying drawings in FIGS. 1-8. In accordance with the purposes of this invention, as embodied and broadly described herein, this invention, in one aspect, relates to method and system that utilizes the EDAR technology to detect characteristics of a gas. The gas can be an exhausted plume from a vehicle or factory plant, leaked gas from an oil well or gas resource, or any unidentified gas from an unknown source.

One particular application of the present invention is to detect emissions of a vehicle as well as the amount of the pollutants emitted from the vehicle.

With the EDAR system, the beam of light emitted from a source is directed downwards, passing through the exhaust plume, toward the surface of a traffic lane of a road on which the vehicle is driven. The transmitted light is then scattered at the surface of the traffic lane. The EDAR system collects the scattered light from the surface of the traffic lane for the detector to receive. Because of the geometry of the remote sensing set up, the EDAR system is always looking down onto the whole plume. This allows the EDAR system to remote sense the entire plume at one time. Further, one can use the optical mass of each measurement across the plume to calculate absolute values. In one embodiment, the height of the back of the vehicle is measured as the top of the plume for calculating the total mass-per-distance of the plume. In another embodiment, by comparing the absorption spectrum of the plume and the background absorption spectrum of which no plume exists, the non-methane hydrocarbons (NMHC) of the plume emitted from a vehicle can be quantified.

Calculating the absolute value of a plume from the optical mass in one column (or cylinder) of gas is straightforward, which is the production of the optical mass multiplied by the area of the column perpendicular to the direction of the beam. For example, if the optical mass is in units of molecules/cm$^2$, and the area perpendicular to a circular column is $\pi r^2$ cm$^2$.

Therefore, the amount of molecules and the column is just an optical mass multiplied by $\pi r^2$.

As shown in FIG. 1, if a plume 110 is sampled with a discrete number of equispaced, infinitesimally thin beams of parallel light 121, the mass-per-distance, d, associated with a beam is estimated by taking its measured optical mass, x, and multiplying it by the beam spacing, w, $$d = w \cdot x, \quad (1)$$

$$x = C \cdot \frac{n}{V} \cdot l. \quad (2)$$

The total mass-per-distance of the plume is then determined by combining each value of d as a Riemann sum:

$$d_{total} = \sum^{N} w \cdot x_i = Nw \cdot \frac{1}{N} \sum^{N} x_i = w_{Total} \cdot x_{Avg}.$$

Figure 2:
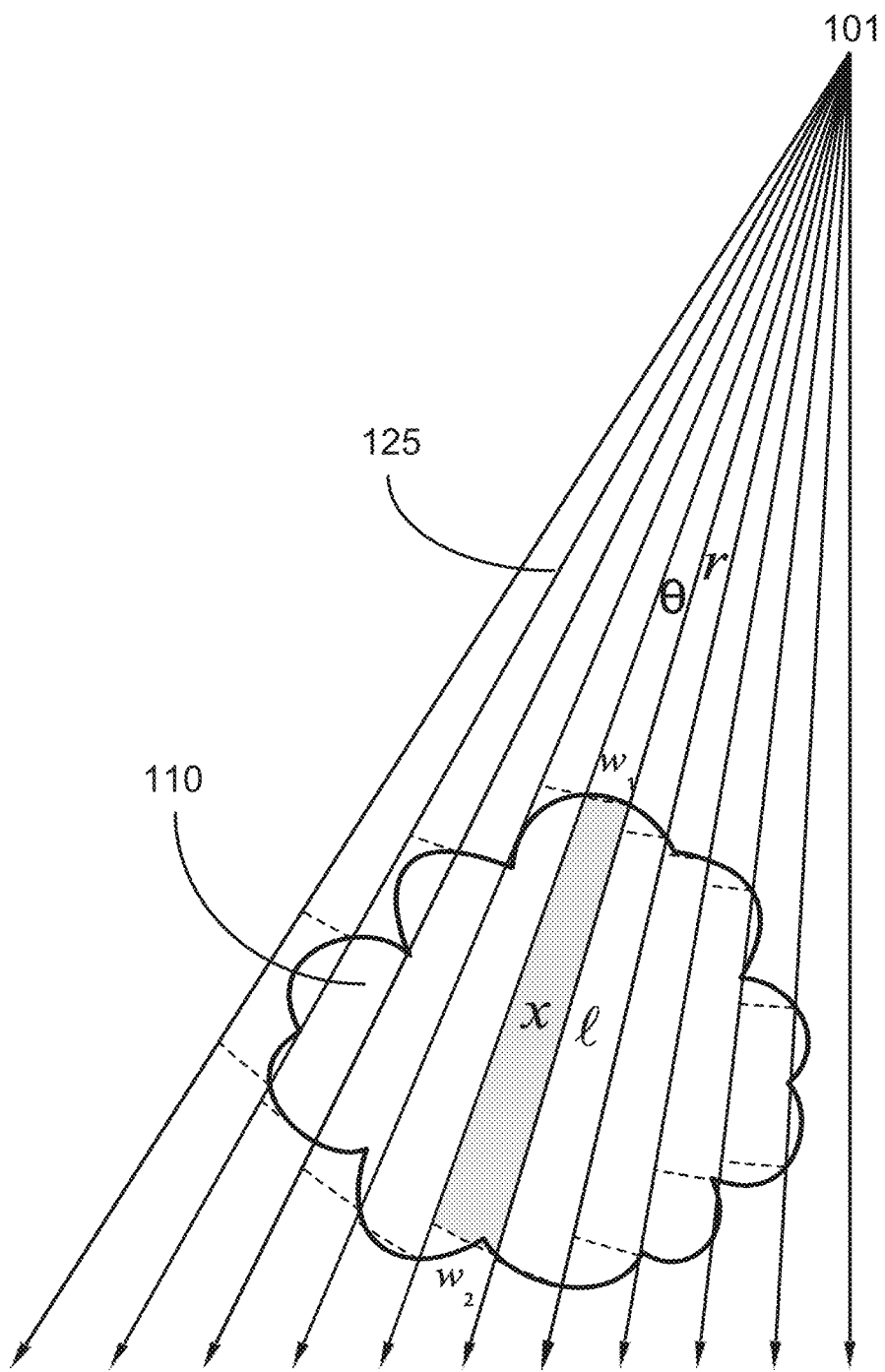
FIG. 2 illustrates schematically a method for quantifying absolute amounts of ingredients of a plume sampled with rays of a light beam according to one embodiment of the invention.

However, in the EDAR system, it scans the road from one point above the road. This in turn creates cone-type geometry of a light beam, as shown in FIG. 2. Calculating the absolute values of the plume using cones instead of columns (cylinders) may become problematic because the area perpendicular to the propagation of the beam is different depending on where it is on the cone. It would be easier if the top of the plume 110 would be known. One could then find the average perpendicular area w of the cone. The average area w would be chosen at that point and the absolute value could be calculated. According to the invention, an average area w somewhere in the middle of the plume 110 is chosen.

As shown in FIG. 2, the same plume 110 is sampled with rays of light 125 originating at a focus (light source) 101. An effective value of the beam spacing (cross-sectional area) w is adapted to multiply the measured optical mass x, so as to obtain the mass-per-distance of the plume 110 that should be the same as that, as expressed in equation (1), in the parallel light beam shown in FIG. 1.

In the exemplary embodiment shown in FIG. 2, the mass-per-distance d for the plume 110 that is mostly uniform over the path length l is obtained by multiplying the density of the gas by the area w between the rays 126 that is filled by the plume 110.

$$d = w \cdot x = C \cdot \frac{n}{V} \cdot \left[\frac{1}{2}\theta \cdot (r+l)^2 - \frac{1}{2}\theta \cdot r^2\right]. \quad (3)$$

Insertion of the optical mass x in equation (2) into equation (3) results in the following relationships:

$$w \cdot C \cdot \frac{n}{V} \cdot l = C \cdot \frac{n}{V} \cdot \frac{1}{2}\theta \cdot [(r+l)^2 - r^2], \quad (4)$$

and $$w = \frac{1}{2}\theta \cdot (2r + l)$$

Accordingly, the effective width w is the width between rays 125 at a distance from the focus 101 to a halfway between the extents of the plume 110.

As an example, assuming that $\theta = 0.68$ mrad, $r = 14$ ft, $l = 4$ in, then $w = 0.116$ in, if $r = 13$ ft, $w = 0.108$ in, $\Delta w = -7\%$, if $r = 15$ ft, $w = 0.123$ in, $\Delta w = +7\%$, $$\Delta w = \frac{r + \Delta r - r}{r} = \frac{\Delta r}{r}.$$

Therefore, to minimize the error, the light source 101 needs to be substantially far away from the plume 110.

Figure 3:
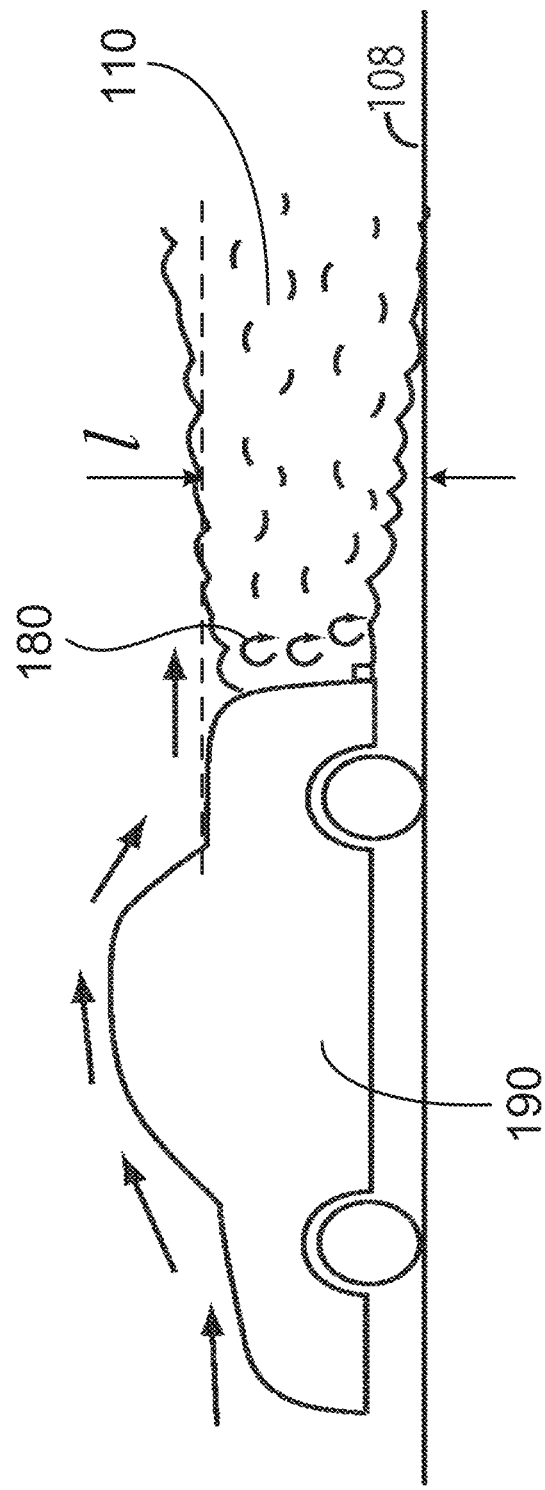
FIG. 3 shows schematically a vehicle and a plume emitted therefrom, which shows the estimated height of the plume.

In addition, the air flowing over a vehicle 190 creates a vortex 180 behind the vehicle 190, as shown in FIG. 3. This vortex 180 mixes the exhaust plume 110. It is known that the top of the plume 110 cannot be much higher than the top of the trunk or roof of the vehicle, just as the vehicle 190 passes. According to the invention, the height of the back of the vehicle 180 is used as an approximation for the distance/from the road surface 108 to the top of the plume 110.

In one aspect, the invention relates to a method for quantifying ingredients of a plume. In one embodiment, the method includes the steps of sweepingly directing a beam of light through the plume to a surface on which the beam of light is scattered; acquiring the scattered light scattered from the surface; and processing the acquired scattered light to determine an amount of ingredients of the plume.

In one embodiment, the processing step comprises the step of calculating an effective width, $w_i$, of each sweeping light beam, wherein the effective width $w_i$ satisfies with the relationship of:

$$w_i = \frac{1}{2}\theta_i \cdot (2r_i + l),$$

wherein $\theta_i$ is an angle of the light beam relative to a direction perpendicular to the road surface, $r_i$ is a distance between the light source and the top of the plume, and l is a thickness of the plume. In one embodiment, the thickness l of the plume is corresponding to a height of the rear of the vehicle that emits the plume. The total mass-per-distance of the plume satisfies with the relationship of:

$$d_{Total} = \sum_{i}^{N} w_i \cdot x_i$$

wherein $x_i$ is an optical mass at each light beam passing through the plume.

In one embodiment, the directing step is performed with a Galvanometer.

Additionally, if one knows the absolute value of a swath of the plume perpendicular to the direction of travel, then one can assume that the absolute amounts of the target molecules were once in the tailpipe at the same time. One can then use the ideal gas equation with ambient temperature (or approximate tailpipe temperature) and pressure to calculate the density, and therefore the number of molecules per unit volume of the air. The absolute amounts could be used to calculate the tailpipe concentrations using a typical 2 inch diameter tailpipe. Therefore, the tailpipe concentrations could be calculated without using stoichiometric equations, which are employed by conventional remote sensing devices to backtrack tailpipe concentrations.

Since there is a large amount of methane already in the earth's atmosphere and natural concentrations can be elevated in certain areas, it is important to separate methane from the other hydrocarbons coming out of the exhaust plume of a vehicle. In one aspect, the invention provides a method for calculating non-methane hydrocarbons in a plume emitted from a vehicle by resolving methane lines on the top of broad features of heavier hydrocarbons in absorption spectra of the plume.

What makes remote sensing with lasers so sensitive is that the narrow line width of a laser line is able to disseminate individual lines from a molecular rotational and vibrational transition. The difference in energy between two adjacent rotational transitions is proportional to the inverse of the moment of inertia of the molecule through the axis of rotation. Therefore, the smaller the moment of inertia about the axis of rotation is, the larger the spacing between rotational lines is.

In one embodiment, the method includes the steps of sweepingly directing a beam of light through the plume to a surface on which the beam of light is scattered; acquiring the scattered light scattered from the surface; and processing the acquired scattered light to determine an amount of ingredients of the plume. The acquired scattered light is processed in terms of an absorption spectrum of the plume. In addition, the method may also include the step of obtaining a background absorption spectrum of which no plume exists. By comprising the step of comparing the absorption spectrum of the plume and the background absorption spectrum, the non-methane hydrocarbons (NMHC) of the plume are quantified.

Figure 4:
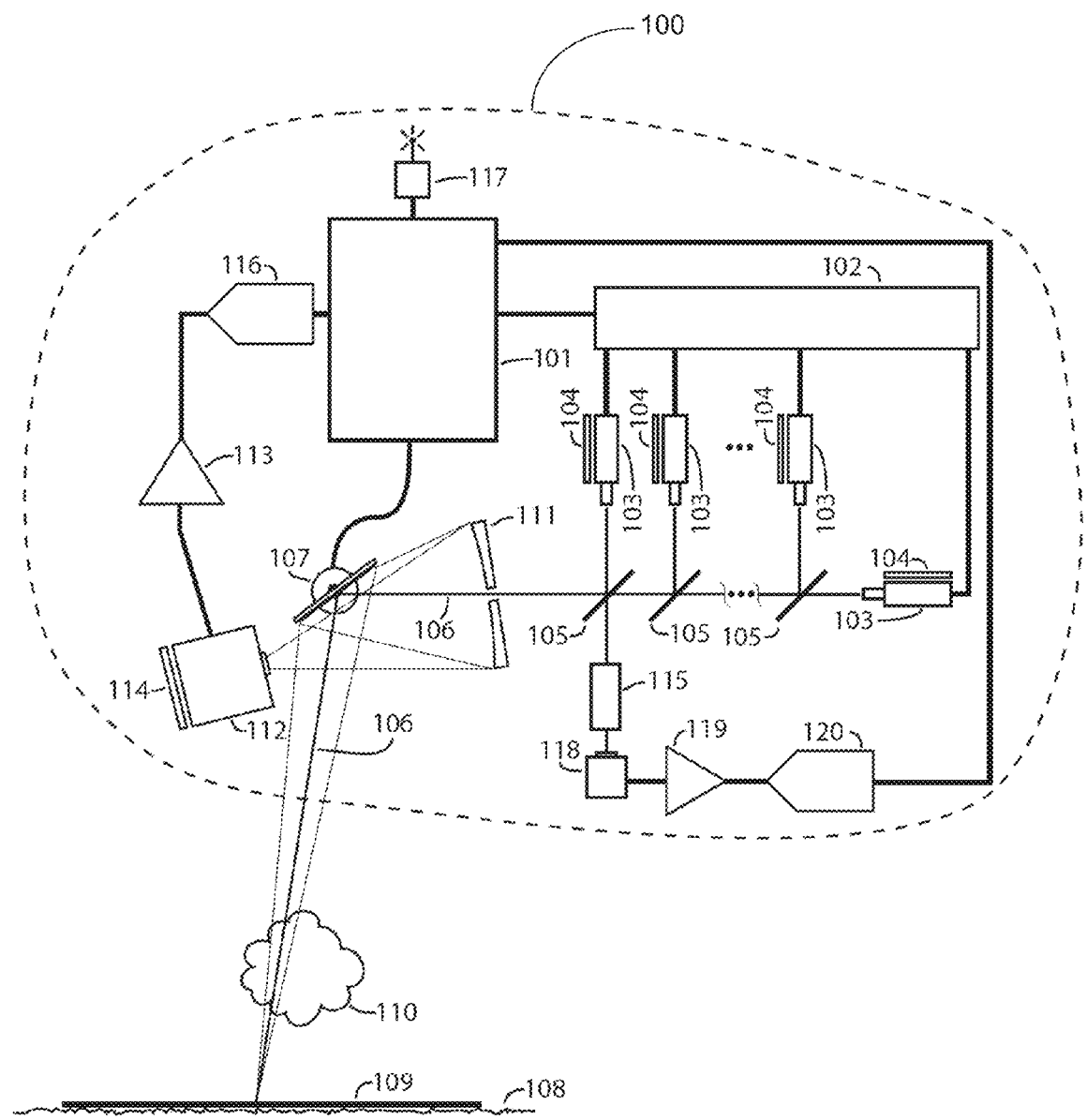
FIG. 4 shows schematically a device for scanning a laser across the roadway according to one embodiment of the invention.

Referring to FIG. 4, a device 100 for quantifying non-methane hydrocarbons in an exhaust plume is shown according to one embodiment of the invention. The device 100 includes coherent light sources or lasers 103, or a tunable laser, and a single-element detector 112. One or more coherent light sources 103 emitting at different selected wavelengths are time-modulated at the laser signal driver and TEC controller 102 by a controller 101. In the case of tunable diode lasers, the wavelengths can be selected by setting the temperature of each laser 103 with a corresponding cooling device 104. In one embodiment, the coherent light sources 103 are the DFB Continuous wave lasers that scan over a small range of wavelengths at usually 20 KHz. Therefore, a measurement is made every $1/1000$ of a sweep. The cooling device 104 is the TEC to cool the lasers 103. The resulting time-modulated light beams are combined with beam-splitters and/or mirrors 105, and are sent through positioning optics 107. In one embodiment, the positioning optics 107 is a Galvanometer with a mirror on top that sweeps across the road 108 at usually 20 Hz. The Galvanometer is also adapted to collect the scattered light and directs it toward the collection mirror 111. The positioned light beam 106 passes through a gaseous plume 110, reflecting off of some substantially reflective material 109. The reflected light beam 106 passes through detection optics 111 and is focused into an optoelectronic detector 112. The electric signal from the detector 112 passes into a low-noise amplifier 113. The detector 112 as well as the amplifier 113 can be placed in a cooling mechanism 114 to increase the sensitivity and stability of the detection. The resulting signal is then passed into an analog-to-digital converter 116. Ultimately the measurement is digitized and processed by the controller 101. The results can be locally displayed or recorded as well as transmitted to a remote location by some communication mechanism 117.

The controller 101 can be a computing device such as an embedded computer in conjunction with application specific digital electronics such as a Field Programmable Gate Array (FPGA).

The coherent sources 103 are typically cooled by a cooling mechanism 104. The cooling mechanism 104 is typically a thermo-electric cooler in conjunction with a temperature measurement device such as a thermistor, which allows the temperature of the source 103 to be precisely controlled electronically with a feedback control system, for example. Adjusting the temperature allows some lasers to be tuned for wavelength. Controlling the temperature has the added benefit of avoiding temperature drift, which can inadvertently modulate the source 103. If the source 103 is substantially stable at a desired wavelength, the cooling mechanism 104 can be omitted simplifying the design as well as lowering its cost.

Since wavelengths of tunable lasers can be swept over many absorption peaks, the controller 101 can pick a peak, which maximizes the signal-to-noise ratio. Usually, it will be a wavelength with the largest absorption and the lowest temperature sensitivity for the measured gas while not coinciding with any other present gases. Also, the system can pick a different wavelength in case it detects is some form of interference at the existing wavelength.

The output power of each coherent source 103 can be regulated as well. This can be done with a current feedback system or a photo-diode feedback system or a combination of the two.

The sources can be modulated by direct electrical stimulation 102 or mechanically using an electrically controlled shutter such as a chopper wheel or a liquid crystal shutter. One method of modulating the light source 103 in the time domain is using a constant frequency waveform such as a sine wave or square wave as well as other more complex, orthogonal patterns. Other time-domain modulation techniques, such as shifting the phase between two sources by 90 degrees, are possible as well.

Time-modulation of the coherent light sources allows the system to ignore background signals or noise by picking a modulation which avoids external light sources. This not only includes any ambient light sources, but also any light emitted by the hot gaseous plume itself. The transmission of light through a plume can be then be consistently measured regardless of the temperature of the plume. Time-modulation also allows the invention to use a single detector 112 by placing each light signal in its own frequency band which can be separated electronically by a demodulation mechanism 115. This reduces the physical complexity of the design as well as replacing high-cost exotic light detection materials with low-cost demodulation electronics or digital computation. Additionally, time-modulation increases the sensitivity of the detector 112 by operating in a band where 1/f noise is lower.

If the coherent light sources 103 are not modulated separately in the time domain, other means can be used to detect each source. For example, the system can use multiple detectors, each tuned to a specific optical wavelength, one for each coherent source. One method is to use an optical filter in conjunction with each detector or even use the detector's natural bandwidth to discriminate each light source. Another method involves changing the polarization of each source and using detectors in conjunction with polarization filters.

The function of the optical combiner 105 is to form the separate coherent beams from the sources 103 into a single light beam 106. The optical combiner 105 can be a fused set of fiber optics or a reversed beam splitter, for example. The optical combiner can be eliminated if only one measurement wavelength is desired or if the sources happen to already be in a single beam or if separate detectors 112 are used for each source 103.

Typically the positioning optics 107 is a spinning or an oscillating mirror connected to a speed-controlled motor, such as a galvanometer. The frequency of the scan determines how fast the light beam is scanned over an area of interest. Also, the amplitude of an oscillating mirror determines the field of view. Also, the galvanometer is inherently synchronized with the detection circuitry. The scan can be a single line 131 or a series of lines 141 in some pattern, which can be used to remotely detect the properties of the gaseous plume of interest. By scanning the light beam 106, the position of the gaseous plume 110 can be determined. Since the speed of the scanning apparatus 107 is controlled, the controlling device 101 can correlate the measurement of the detector 112 with the position of the beam 106.

The reflector 109 can be made of various materials. Retro-reflective tape or paint can be used, for example. Alternatively, an array of mirrored corner cubes can be attached to the roadway. Other aspects over the choice of material involve whether or not the installation is temporary or permanent. The additional reflector 109 can be omitted if the roadway 108 or other pre-existing background feature is substantially reflective so that a suitable signal-to-noise ratio is achieved with the plume 110 of interest. The reflective surface 109 can be omitted altogether if the source and detector are separated such that the plume 110 is between the two. This requires two separate controllers 101 and possible a phase-lock loop or other means to synchronize the two devices.

Since the reflective surface 109 is on a roadway 108 or some other uncontrolled area given to environmental wear-and-tear, it is reasonable to assume that the reflection will not be uniform over the area of the surface. Because this invention divides the measured region into substantially small beams 106, the reflection over any one beam 106 will be mostly constant. Also, since the measurements can be made relative to a baseline measurement 203, the constant sources of attenuation will divide out of the calculations.

Since this embodiment uses an external reflective surface 109, both the modulated sources 103 as well as the detector 109 can be physically together 118, and controlled by a single controller 101. One advantage of this scheme is that since the modulated sources and the detector can be controlled centrally, the modulated sources can be synchronized with the detector electronics. This eliminates the need for a phase-lock-loop or other synchronizing mechanism in the detector electronics.

The detection section of this embodiment includes focusing optics 111 as well as an electro-optical detector 112 connected to a low-noise amplifier 113. The focusing optics 111 allows the embodiment to image a large area, preferable large enough to see the entire plume of interest 110. The detector 112 can be a semi-conductor photodiode or a thermopile or any such sensitive detection device. The detector is made of a material that can detect light in the desired wavelengths. The low-noise amplifier 113 can consist of any appropriate analog signal processing electronics able to suitably extract the signal of interest from the detector 112.

Conventionally, parallel light sources are utilized to measure gaseous plumes, which is disadvantageous because it requires the measurement system to be as large as the plume itself. This can be impractical if the plume is very large such as one from a smoke stack. This embodiment of the invention uses focused light which allows the entire system 118 to be substantially smaller than the plume 110 itself or the region of interest and fit in a compact and practical space. This potentially makes the device unobtrusive and portable.

The optoelectronic detector 112 as well as the low-noise amplifier 113, can be cooled 114 to increase the sensitivity of the detection. Controlling the temperature has the added benefit of making the detector 112 more stable, eliminating unwanted drift in the measured signal. Various cooling techniques are possible including thermo-electric coolers, a Dewar flask containing some cryogenic liquid, or a Stirling engine. If the existing detector element 112 and the low-noise amplifier 113 are substantially sensitive enough, the cooling mechanism 114 can be omitted altogether saving cost and simplifying the design.

While using only single broadband detector 112 is desirable to keep the system simple, a series of narrow-band or otherwise band-limited detectors can be used if there isn't any one practical detector with contiguous band which contains all of the wavelengths of interest.

One aspect of the present invention relates to a device for detecting characteristics of a gas. In one embodiment, the device includes: a light source configured to emit a beam of light through the gas to a target surface on which the beam of light is scattered; a detector configured to acquire the scattered light scattered from the surface; and a processor configured to process the acquired scattered light to determine the characteristics of the gas. In certain embodiments, the characteristics of the gas include at least one of a temperature of the gas and an amount of at least one ingredient of the gas.

In one embodiment, the gas is an exhaust plume, and an optical path between the light source and the detector substantially encompasses an entire space occupied by the exhaust plume. In one embodiment, a diameter of the beam of light is relatively large in comparison to the entire space occupied by the exhaust plume such that a cylindrical space having the diameter and formed along the optical path substantially encompass the entire space occupied by the exhaust plume. In one embodiment, the device further includes a returning optics positioned in the optical path for extending the optical path to passes through the exhaust plume multiple times, such that the optical path substantially encompasses the entire space occupied by the exhaust plume.

As discussed above, conventionally, a non-dispersive infrared system usually uses an infrared beam 2 to 3 inches in diameter. The beam is directed across the road and reflected back through a series of mirrors. The system therefore only senses a percentage of the gases in the entire cross-section of the plume. The system then uses ratios to carbon dioxide to calculate the combustion equation. The combustion equation then gives you tailpipe percentages. Therefore, in order to get grams per mile one must calculate the vehicle specific power (VSP) and know model and make of the vehicle.

On the other hand, if the beams were much larger or there were more beams, then one could safely assume, at least in the beginning of a vehicle passing a device, the entire plume may be detected. The retrieved absorption would include all the molecules in a vertical section of the exhaust plume. This vertical section of the exhaust is what the vehicle expelled at some time $\Delta T$ while traveling down the road. From this one can calculate grams for miles directly, without the use of the combustion equation or vehicle specific power.

Figure 5:
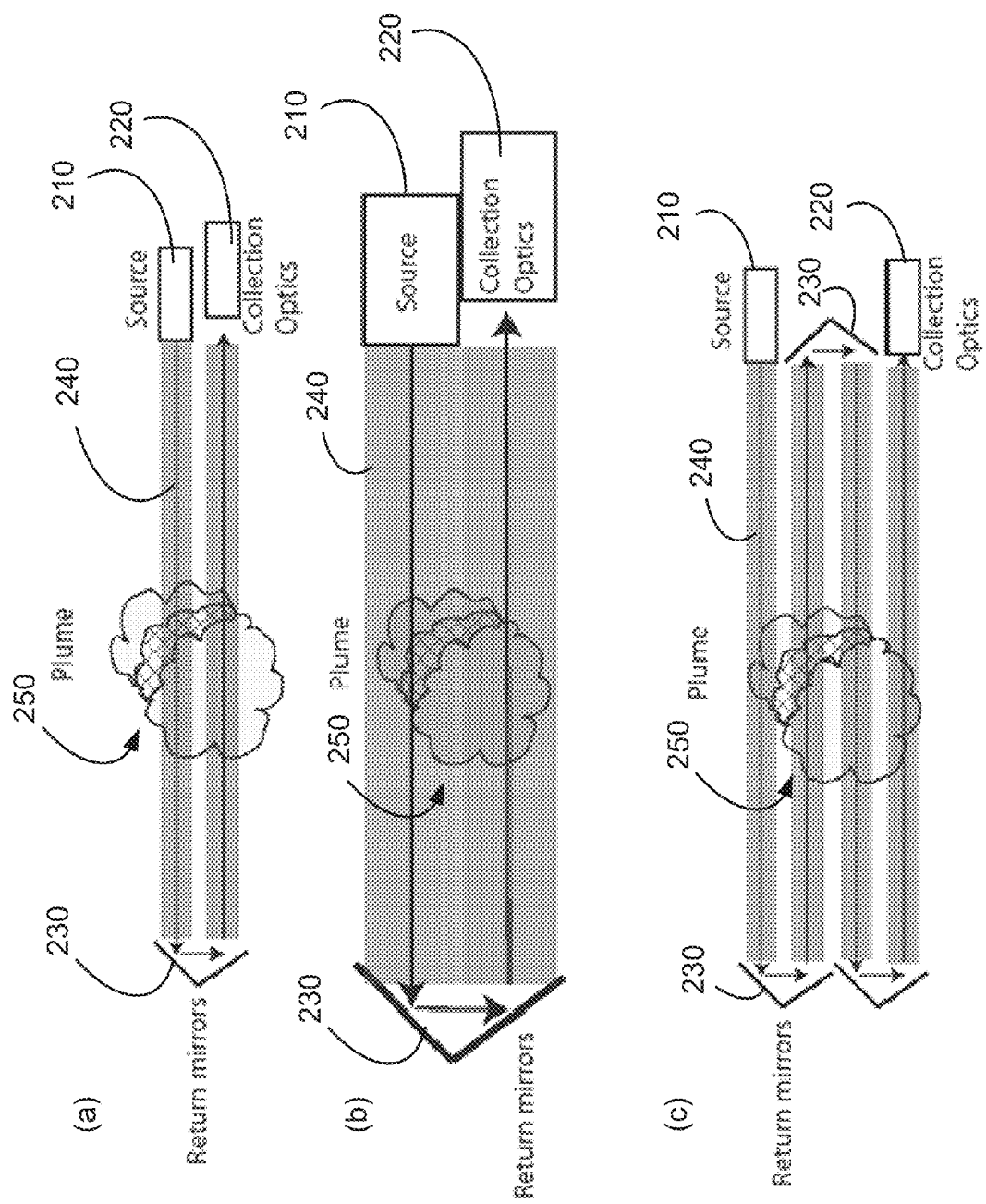
FIG. 5 shows schematically examples (a)-(c) of the beam of light passing the exhaust plume according to embodiments of the invention.

FIG. 5 shows schematically examples of the beam of light passing the exhaust plume according to embodiments of the invention, where the relative size or diameters of the beams 240 and the optical paths of the beams are different as compared to the size of the exhaust plume 250. FIG. 5(a) shows an example where the diameter of beams 240 is relatively small compared to the exhaust plume 250, and the beam path from the light source 210 to the return mirrors 230 and the beam path from the return mirrors 230 back to the collection optics are not aligned next to each other. Thus, there is a gap between the beams as they traverse back and forth.

In comparison, FIG. 5(b) shows an example where the diameter of beams 240 is relatively large in comparison to the entire space occupied by the exhaust plume 250. In this way, the relatively large beams 240 traversing back-and-forth across the optical path, such that the beams 240 are large enough to encompass the entire space occupied by the exhaust plume 250 for a short time before it disperses beyond the boundaries of the beams 240. More precisely, the beam 240 is in a shape of a cylindrical space, which has the diameter and formed along the optical path of the beam 240, to substantially encompass the entire space occupied by the exhaust plume 250. During the time the exhaust plume 250 is within the boundaries of the beam 240, the system measures absolute amounts. If the exhaust plume 250 is not dispersed beyond the boundaries of the beams 240, all the molecules that the car left behind at some time over $\Delta T$ may be measured. Thus, the grams per mile may be calculated directly.

FIG. 5(c) shows a multi-pass system that will encompass the entire exhaust plume 250. As shown in FIG. 5(c), the returning optics include multiple return mirrors positioned in the optical path of the beam 240 for extending the optical path to passes through the exhaust plume 250 multiple times, such that the optical path substantially encompasses the entire space occupied by the exhaust plume 250 without increasing the size of the beam 240. The passes will also make the system more sensitive because of the increase in the optical path length. Gaps between the beams become less important due to interpolation.

It should be noted that one way to test if the exhaust plume 250 has not dispersed outside the beams is by using an infrared camera with a $CO_2$ narrow band filter to measure the size of the exhaust plume 250.

In one aspect of the invention, the EDAR system may be used to remotely sense vehicle emissions on multi-lane roads.

In one embodiment, the geometry of EDAR system looks down on a whole lane of traffic allowing it to make measurements on multi-lane roads. When there is no traffic in the target lane or adjacent lanes the graph of the amount of the target gases across the lane should be zero or flat in theory. If the graph is not flat or zero when there is no traffic in the target lane, there must be an interfering exhaust plume coming from adjacent lanes. When the EDAR system attempts to measure an exhaust plume in the target lane, the graph obtained by the EDAR system is not flat or zero if there is an exhaust plume from the edges of the scan, which is not the target plume on the target lane. This is shown in FIG. 6.

Figure 6:
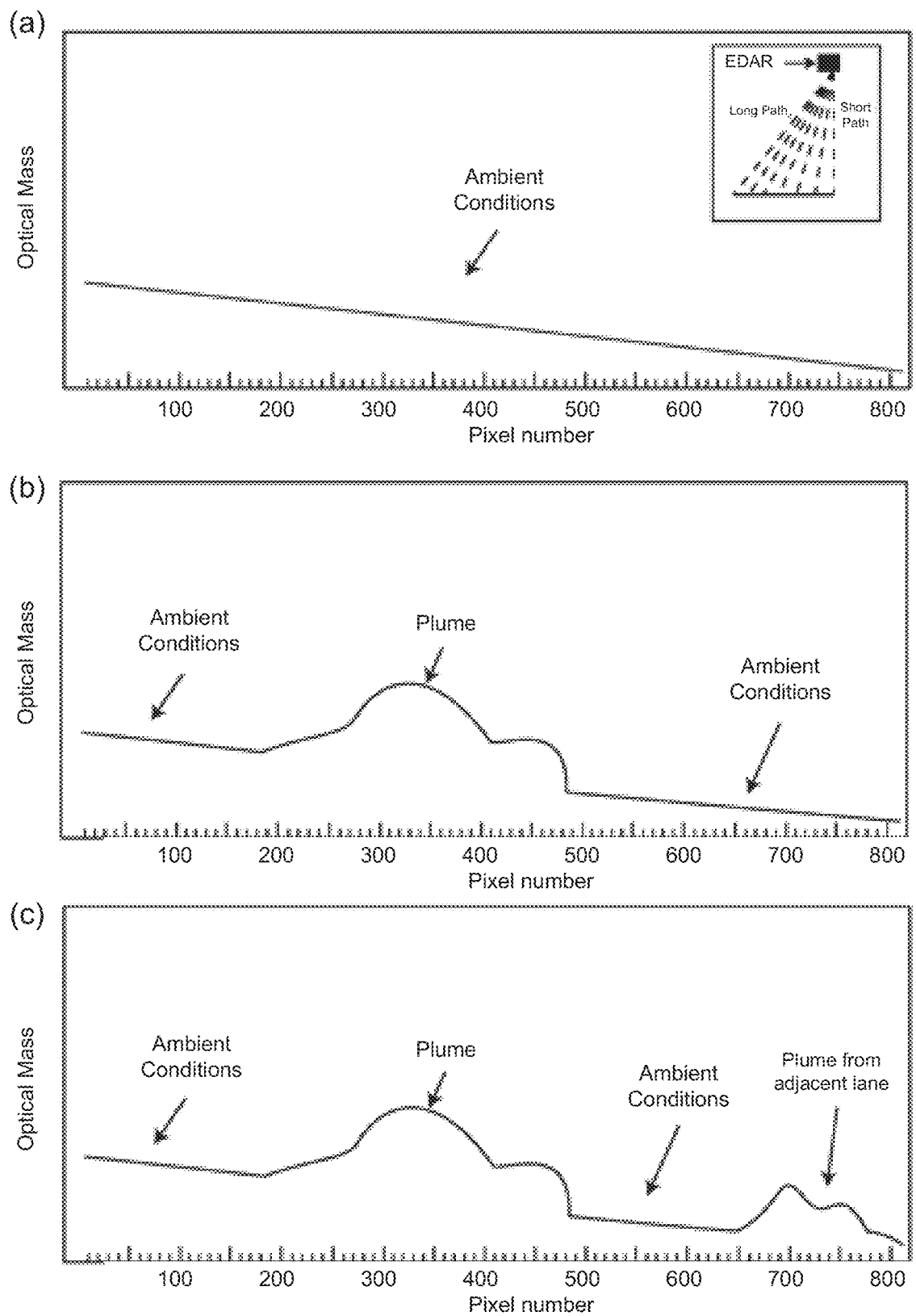
FIG. 6 shows schematically a plurality of lines showing the relationship of optical mass to pixel number according to embodiments of the invention, where (a) shows the ambient conditions; (b) shows that an exhaust plume exists; and (c) shows that two exhaust plumes exist.

FIG. 6 shows schematically a plurality of lines showing the relationship of optical mass to pixel number according to embodiments of the invention, where (a) shows the ambient conditions; (b) shows that an exhaust plume exists; and (c) shows that two exhaust plumes exist. In one embodiment, as the EDAR system scans back and forth across the target lane, the EDAR system calculates the optical mass or mole/cm² for four gases. The distance it takes to measure all four gases as the EDAR system scans is designated as a pixel. Usually, pixels are a couple of millimeters (mm). The optical mass is angled because of the increase in path length as EDAR scan further away, as shown in FIG. 6(a). The optical mass line will remain flat as long as the target gas is well mixed. When a vehicle passes it leaves behind an exhaust plume, as shown in FIG. 6(b). In certain embodiments, an additional exhaust plume from an adjacent lane may interfere with the exhaust plume in the target lane. Once an exhaust plume from the adjacent lane sneaks into to the target lane, adjustments or rejections may be determined.

As shown in FIG. 6(b), the geometry of EDAR system may be used to measure ambient concentrations away from the exhaust plume at essentially the same time it measures the exhaust plume. If the measurements away from the targeted plume indicate lingering gases from the adjoining lane, as shown in FIG. 6(c), then the measurement becomes suspect. Then the operator of the EDAR system can then take actions to compensate for the interfering exhaust or throw out the current measurement.

If the exhaust plume from the previous car dissipates, it becomes well mixed with the ambient atmosphere. Generally this takes only a matter of seconds. Even though ambient amounts of carbon monoxide (CO), carbon dioxide ($CO_2$) and nitrous oxide (NO) are above normal levels due to the amount of traffic, as long as it is well mixed the EDAR system can subtract out ambient amounts to only retrieve the amounts coming for the targeted plume. This minimizes negative readings seen in other systems.

The graph of EDAR absolute values measurements across the road is flat if exhaust gases are well mixed in the field of view. The optical mass is angled because of the increase in path length as EDAR scan further away, as shown in FIG. 6(a). FIG. 6(b) shows a typical scan of an exhaust plume of a passing vehicle. As soon as gases from a source outside the lane drift into the lane that the EDAR system is measuring, the absolute value graph is no longer straight line and the absolute values measurements detects a secondary plume, as shown in FIG. 6(c). In one embodiment, as long as this secondary plume does not drift into the primary plume it can be subtracted out and the measurement can be saved. Alternatively, if there is any indication of a secondary plume, the whole measurement can be thrown out. If the secondary plume is small enough it can be just ignored.

In one embodiment, the detecting function of the EDAR system may be expanded to detect multiple lanes of the road at the same time. In this case, each lane of the road corresponds to a group of the pixels, as shown in FIG. 6(c). Based on the exhausted plume detector corresponding to the pixel number, the location of the exhausted plume on the lanes of the multi-lane road may be determined.

In one aspect, the EDAR system may be used to measure the temperature of the gas using the coefficient of temperature dependence of the air-broadened half-widths.

As discussed above, the emissions mitigation systems on vehicles usually take a minute or so to warm up, but can take much longer. Emissions testing stations often have failing cars drive around and come back to warm up their vehicles more. The hotter vehicles often pass their emissions test. Thus, current remote sensing devices must measure the same vehicle at least 3 times at different locations to justify marking it as a dirty vehicle. The chance of the same vehicle being cold in different locations and times are remote. The use of the EDAR system may eliminate this 3-times measuring requirement by measuring the exhaust temperature only once.

Temperature affects both the line strengths in the line broadening of an infrared absorption line. The dependency of Lorentz broadening on temperature is:

$$b_L^0(T) = b_L^0(T_0)(T_0/T)^n \tag{5}$$

where T is the temperature, n is a coefficient of temperature dependence of an air-broadened half-width, $T_0$ is a standard temperature, and $b_L^0(T_0)$ is a standard half-width at half maximum (HWHM) corresponding to the standard temperature. The zero superscript denotes it is the half-width at some standard pressure. The air-broadening half-width is calculated using typical ambient concentrations. In the case of exhaust gases self-broadening coefficients will be taken into account.

$$b_L^0(T) = b_{L,air}^0(T)(1-\chi) + b_{L,self}^0(T)\chi$$

where $\chi$ is the volume mixing ratio.

The HWHM refers to one half of the full width of the absorption line at half of the maximum (HWHM) of the absorption line. The lines the EDAR system measures will narrow at hotter vehicle exhaust temperatures compared to ambient temperatures. The HWHM of an absorption line is independent of line strength. The HWHM of the line may be measured, and if the measured HWHM does not agree with the ambient temperature calculations of HWHM, the exhaust plume is likely a plume of elevated temperature. The exhaust temperature may be calculated using the measured HWHM as follows.

$$T_{gas} = T_0 \left[ \frac{b_L^0(T_0)}{b_L^0(T_{gas})} \right]^{\frac{1}{n}} \quad (6)$$

where $T_{gas}$ is the temperature of the gas, and $b_L^0(T_{gas})$ is the obtained HWHM.

In certain embodiments, exhaust gases with low ambient concentration, such as carbon monoxide and nitric oxide can be used to increase sensitivity. Ambient amounts of carbon dioxide contribute a larger percentage to the HWHM than the aforementioned molecules. Since, ambient amounts are at ambient temperatures, this makes carbon dioxide lines average HWHM less sensitive to temperature change.

A typical case is where the HWHM will changes 10% as the temperature changes 40° C.

The dependency of Doppler broadening can be neglected at atmospheric pressures in an overwhelming majority of cases. The Doppler broadening coefficient is:

$$b_D = \left(\frac{v_0}{c}\right)\left[\frac{2kN_A T\ln 2}{M}\right]^{\frac{1}{2}} \quad (7)$$

Figure 7:
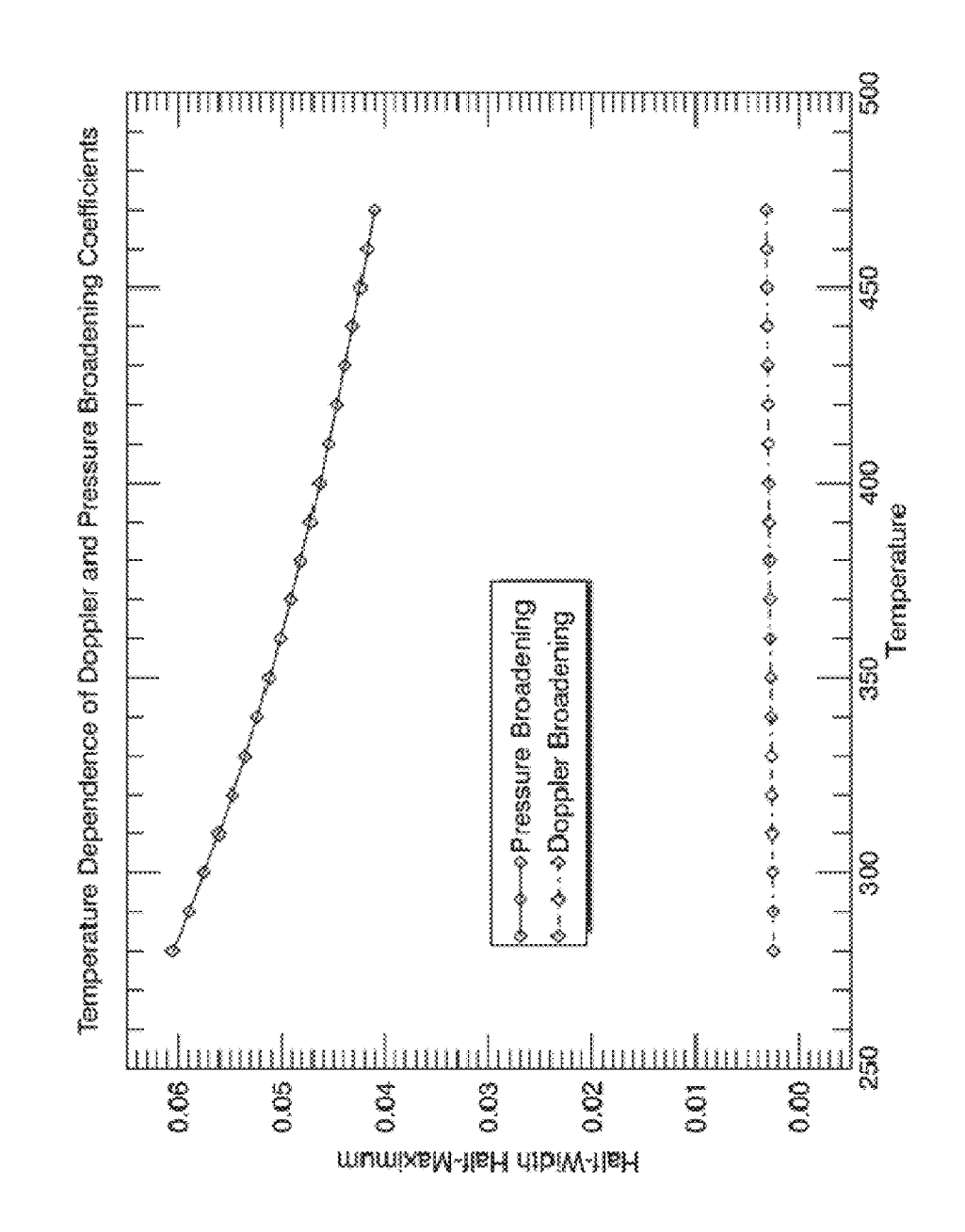
FIG. 7 shows a temperature dependence of pressure and Doppler broadening according to one embodiment of the invention.

FIG. 7 shows a temperature dependence of pressure and Doppler broadening according to one embodiment of the invention. As shown in FIG. 7, the straight line shows the pressure broadening, and the dotted line shows the Doppler broadening. Typically pressure broadening is an order of magnitude greater than Doppler broadening at atmospheric surface pressures. Also, the pressure-broadening coefficient is much more dependent on temperature than Doppler broadening coefficient at typical vehicle exhaust temperatures. This allows us to calculate the temperature of the exhaust by only using the pressure broadening formula, as disclosed in Equation (6). In certain embodiments, the column abundances and the temperature of the target gas may be measured at the same time with the same laser, thereby reducing costs.

In another aspect, the EDAR system may be used to remotely sense methane or other gas leaks at natural gas or oil drill sites.

EPA's new air rules for the oil & natural gas industry will come into effect nationwide in 2015. Equipment and processes at the well site may be covered by requirements under the New Source Performance Standards (NSPS) for volatile organic compounds, and the National Emissions Standard for Hazardous Air Pollutants (NESHAP) for oil and natural gas production. EPA has made a number of changes to these final rules based on public comments.

NSPS requirements for new & modified pneumatic controllers have changed. Pneumatic controllers are automated instruments used for maintaining a condition such as liquid level, pressure, and temperature at wells and gas processing plants, among other locations in the oil and gas industry. These controllers often are powered by high-pressure natural gas and may release gas (including VOCs and methane) with every valve movement, or continuously in many cases as part of their normal operations.

According to the new rules for controllers used at a well site, the gas bleed limit is 6 cubic feet of gas per hour at an individual controller.

Current systems that detect gas leaks do not quantify the leaks. Leaks are usually detected using an infrared camera then sniffers systems are brought in to give absolute amounts of these leaks such as 6 ft³/hr. Infrared cameras are designed to locate the leaks, but not to quantify them with any accuracy. Sniffer systems are usually hand held wands connected to a backpack. A worker puts the wand near the leak and suck in an amount of ambient air much larger than the leak. The amount of methane is measured using a detection system inside of the backpack. From this a flow rate of gas from the leak can be calculated. Workers cannot always reach the locations of the leaks. Leaks are not always so localize where the sniffers can engulf the entire leak The EDAR system can detect and measure absolute amounts of leaks simultaneously. EDAR was developed to measure absolute amounts of vehicle exhaust. A modified system has been developed to measure flow rates or absolute amounts coming from individual controllers or actuators at a well site. Flow rates of leaks can be calculated using a scanning laser across the plume of the leak. The direction and ambient winds can be controlled through an artificial wind source such as fans. The flow of the leaking gas can be directed approximately perpendicular to the location of the EDAR system. The EDAR system can then measure absolute amounts similar to vehicle exhaust remote sensing. By measuring the location were the leak plume crosses a scanning laser and knowing the direction of the ambient wind, one and discern the approximate site of the leak.

Figure 8:
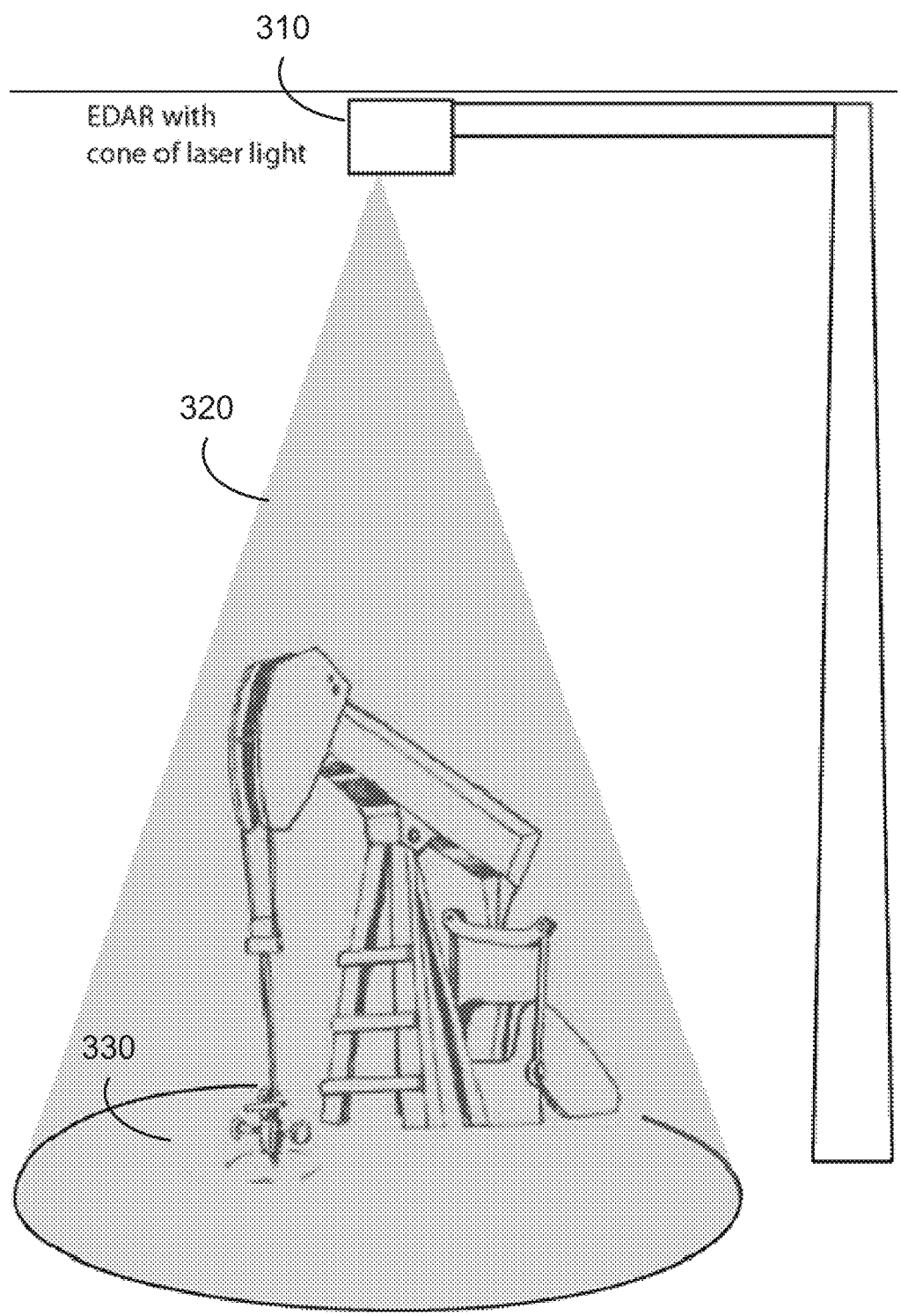
FIG. 8 shows schematically a device for sensing gas leak according to one embodiment of the invention.
Figure 9:
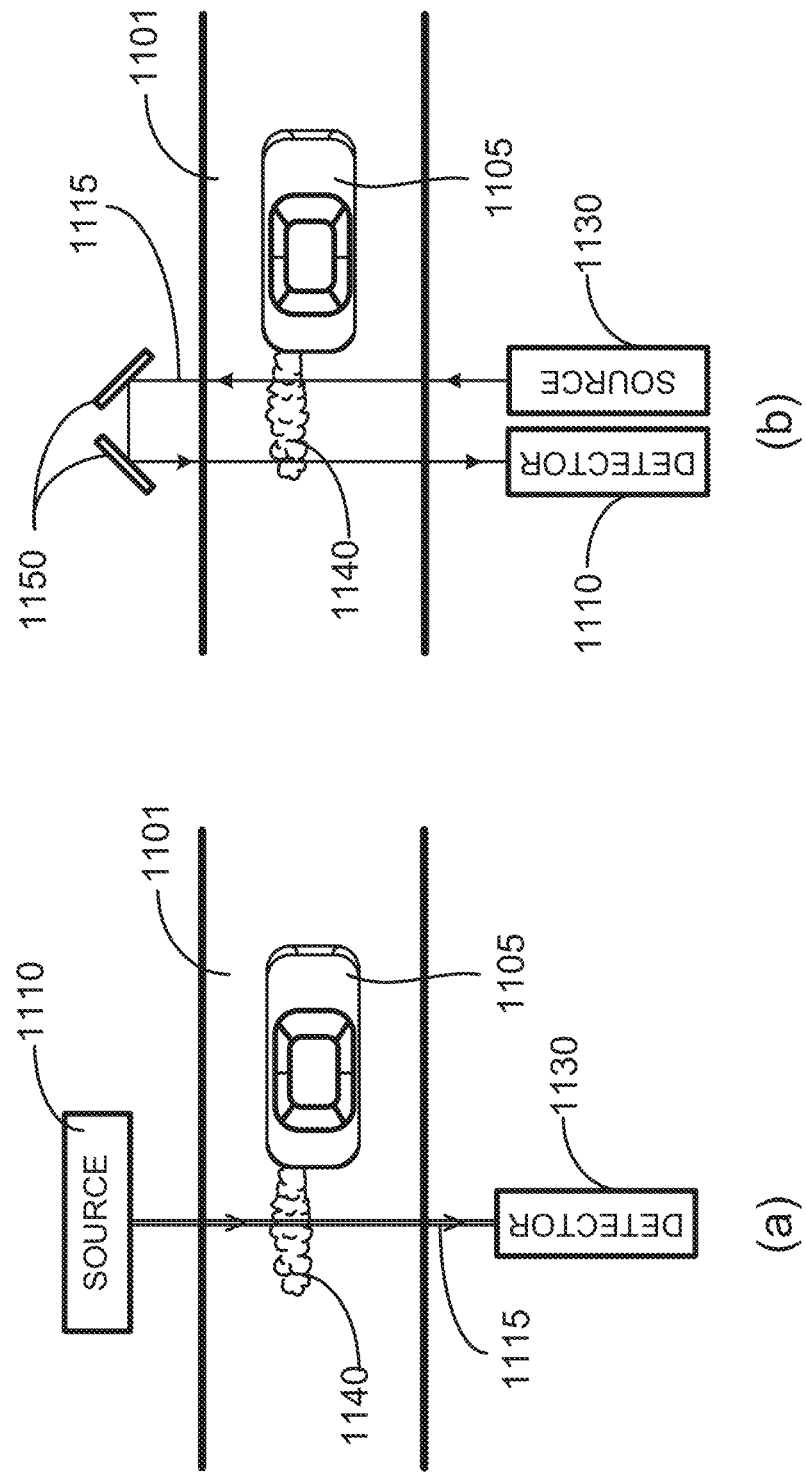
FIG. 9 shows schematically a conventional device for remote sensing of vehicle emission.

A cone system could be used to measure the leaks in an active well site shown in FIG. 8. As shown in FIG. 8, the EDAR system 310 can be fitted with an X-Y galvanometer or a spinning mirror to spin-sweepingly direct the beam of light, such that the optical path of the beam may form a cone geometry 320 to cover the target space 330. Fans from different angles can blow ambient air across the structure. The leaking gas would then exit the cone geometry 320 perpendicular to the scanning lasers. This would allow for the measurement of the flow rate of the leaks and there location.

In sum, the invention, among other things, recites a remote sensing device that uses the EDAR technology. The beam of light emitted from a source is directed downwards, transmitting through the gas, toward the target surface. The transmitted light is then scattered at the target surface. A collecting optics is used to collect the scattered light from the target surface. The collected light is delivered to the detector for analyzing the components and providing the characteristics of the gas, which may include at least one of a temperature of the gas and an amount of at least one ingredient of the gas. In one embodiment, the device may be used to detect the entire space occupied by the exhaust plume by adjusting the size of the beam or the optical path of the beam. In one embodiment, the device may be used to detect exhaust plumes on a multi-lane road. In one embodiment, the device may be used to detect the temperature of the gas using HWHM. In one embodiment, the device may be used to detect gas leak of a natural gas or an oil drill site.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A method for detecting characteristics of a gas, comprising:
   (a) sweepingly directing a beam of light through the gas to a target surface on which the beam of light is scattered;
   (b) acquiring the scattered light scattered from the target surface; and
   (c) processing the acquired scattered light to determine the characteristics of the gas, wherein the characteristics of the gas comprise at least one of a temperature of the gas and an amount of at least one ingredient of the gas,
      wherein the gas comprises one of an exhausted plume from a vehicle or factory plant, leaked gas from an oil well or gas resource, and unidentified gas from an unknown source; and
      wherein the target surface is one of a road surface of a road having at least one lane, a drill surface of oil well or gas resource and a surface having the unidentified gas; and
      wherein the acquiring step comprises:
      acquiring an image from the scattered light; and
   wherein the processing step comprises:
      obtaining a plurality of pixels from the acquired image, each pixel representing a pixel area of the road, wherein each of the at least one lane of the road correspond to a group of the pixels;
      characterizing an absorption rate of light of each pixel from the acquired image;
      calculating optical mass of each pixel from the characterized absorption rate of the pixel; and
      for each of the at least one lane, identifying whether the gas exists on the lane based on the optical mass of the corresponding group of the pixels.

2. A method for detecting characteristics of a gas, comprising:
   (a) sweepingly directing a beam of light through the gas to a target surface on which the beam of light is scattered;
   (b) acquiring the scattered light scattered from the target surface; and
   (c) processing the acquired scattered light to determine the characteristics of the gas, wherein the characteristics of the gas comprise at least one of a temperature of the gas and an amount of at least one ingredient of the gas,
      wherein the gas comprises one of an exhausted plume from a vehicle or factory plant, leaked gas from an oil well or gas resource, and unidentified gas from an unknown source; and
      wherein the target surface is one of a road surface of a road having at least one lane, a drill surface of oil well or gas resource and a surface having the unidentified gas; and
      wherein the processing step comprises:
   (a) characterizing an absorption line from the acquired scattered light;
   (b) obtaining a half-width at half-maximum (HWHM) of the absorption line; and
   (c) determining the temperature of the gas from the obtained HWHM with a relationship of:

$$T_{gas} = T_0 \left[ \frac{b_L^0(T_0)}{b_L^0(T_{gas})} \right]^{\frac{1}{n}},$$

wherein $T_{gas}$ is the temperature of the gas, $T_0$ is a standard temperature, $b_L^0(T_0)$ is a standard HWHM corresponding to the standard temperature, $b_L^0(T_{gas})$ is the obtained HWHM, and n is a coefficient of temperature dependence of an air-broadened halfwidth.

3. The method of claim 2, wherein the HWHM is obtained from the absorption line of the exhausted plume with low ambient concentration, and wherein the exhausted plume with low ambient concentration is carbon monoxide (CO) or nitric oxide (NO).

4. A method for detecting characteristics of a gas, comprising:
   (a) sweepingly directing a beam of light through the gas to a target surface on which the beam of light is scattered;
   (b) acquiring the scattered light scattered from the target surface; and
   (c) processing the acquired scattered light to determine the characteristics of the gas, wherein the characteristics of the gas comprise at least one of a temperature of the gas and an amount of at least one ingredient of the gas,
      wherein the gas comprises one of an exhausted plume from a vehicle or factory plant, leaked gas from an oil well or gas resource, and unidentified gas from an unknown source; and
      wherein the target surface is one of a road surface of a road having at least one lane, a drill surface of oil well or gas resource and a surface having the unidentified gas; and
      wherein the directing step comprises:
      spin-sweepingly directing the beam of light along an optical path to the target surface such that the optical path spin-forms a cone geometry covering the target surface.

5. The method of claim 4, wherein the processing step comprises:
   (a) processing the acquired scattered light to obtain information corresponding to the cone geometry;
   (b) identifying whether the gas exists in the cone geometry based on the information corresponding to the cone geometry; and
   (c) if the gas exists, determining at least one of a location of the gas on the target surface, a flow rate of the gas, at least one ingredient of the gas, and an absolute amount of the gas.

6. A device for detecting characteristics of a gas, comprising:
- (a) a light source configured to emit a beam of light through the gas to a target surface on which the beam of light is scattered;
- (b) a detector configured to acquire the scattered light scattered from the surface; and
- (c) a processor configured to process the acquired scattered light to determine the characteristics of the gas, wherein the characteristics of the gas comprise at least one of a temperature of the gas and an amount of at least one ingredient of the gas,
- (d) a positioning optics configured to sweepingly direct the beam of light emitted by the light source through the gas to the target surface,
    - wherein the gas comprises one of an exhausted plume from a vehicle or factory plant, leaked gas from an oil well or gas resource, and unidentified gas from an unknown source; and
    - wherein the target surface is one of a road surface of a road having at least one lane, a drill surface of oil well or gas resource and a surface having the unidentified gas.

7. The device of claim 6, wherein the detector is configured to acquire an image from the scattered light, and the processor is configured to process the acquired image to perform functions of:
- (a) obtaining a plurality of pixels from the acquired image, each pixel representing a pixel area of the road, wherein each of the at least one lane of the road correspond to a group of the pixels;
- (b) characterizing an absorption rate of light of each pixel from the acquired image;
- (c) calculating optical mass of each pixel from the characterized absorption rate of the pixel; and
- (d) for each of the at least one lane, identifying whether the gas exists on the lane based on the optical mass of the corresponding group of the pixels.

8. The device of claim 6, wherein the processor is configured to determine the temperature of the gas by:
- (a) characterizing an absorption line from the acquired scattered light;
- (b) obtaining a half-width half-maximum (HWHM) of the absorption line; and
- (c) determining the temperature of the gas from the obtained HWHM with a relationship of:

$$T_{gas} = T_0 \left[ \frac{b_L^0(T_0)}{b_L^0(T_{gas})} \right]^{\frac{1}{n}},$$

wherein $T_{gas}$ is the temperature of the gas, $T_0$ is a standard temperature, $b_L^0(T_0)$ is a standard HWHM corresponding to the standard temperature, $b_L^0(T_{gas})$ is the obtained HWHM, and n is a coefficient of temperature dependence of an air-broadened half-width.

9. The device of claim 8, wherein the HWHM is obtained from the absorption line of the exhausted plume with low ambient concentration, and wherein the exhausted plume with low ambient concentration is carbon monoxide (CO) or nitric oxide (NO).

10. The device of claim 6, wherein the positioning optics is configured to spin-sweepingly direct the beam of light through the gas to the target surface such that an optical path between the positioning optics and the target surface spin-forms a cone geometry covering the target surface.

11. The device of claim 10, wherein the positioning optics comprises an X-Y galvanometer or a spinning mirror.

12. The device of claim 10, wherein the processor is configured to perform functions of:
- (a) processing the acquired scattered light to obtain information corresponding to the cone geometry;
- (b) identifying whether the gas exists in the cone space based on the information corresponding to the cone geometry; and
- (c) if the gas leak exists, determining at least one of a position of the gas on the target surface, a flow rate of the gas, at least one ingredient of the gas, and an absolute amount of the gas.

* * * * *